United States Patent
Fukui et al.

(10) Patent No.: US 11,633,301 B2
(45) Date of Patent: Apr. 25, 2023

(54) MEDICAL INSTRUMENT, MEDICAL DEVICE, METHOD OF MANUFACTURING MEDICAL INSTRUMENT, AND METAL ARTICLE

(71) Applicant: HATTA KOGYO CO., LTD, Osaka (JP)

(72) Inventors: Junichi Fukui, Osaka (JP); Kenzo Sumiya, Osaka (JP)

(73) Assignee: Hatta Kogyo Co., Ltd., Sakai (JP)

( * ) Notice: Subject to any disclaimer, the term of this patent is extended or adjusted under 35 U.S.C. 154(b) by 0 days.

(21) Appl. No.: 17/134,036

(22) Filed: Dec. 24, 2020

(65) Prior Publication Data

US 2021/0113370 A1   Apr. 22, 2021

Related U.S. Application Data

(63) Continuation of application No. PCT/JP2019/026112, filed on Jul. 1, 2019.

(30) Foreign Application Priority Data

Jun. 29, 2018   (JP) .............................. JP2018-124201

(51) Int. Cl.
*A61F 9/007*   (2006.01)
*A61B 17/285*   (2006.01)
(Continued)

(52) U.S. Cl.
CPC ............ *A61F 9/007* (2013.01); *A61B 17/285* (2013.01); *A61B 17/3201* (2013.01); *C23C 8/22* (2013.01);
(Continued)

(58) Field of Classification Search
CPC ........ A61F 9/007; A61F 9/001; A61B 17/285; A61B 17/3201; A61B 17/28; A61B 17/29;
(Continued)

(56) References Cited

U.S. PATENT DOCUMENTS 5,292,330 A * 3/1994 Shutt .............. A61B 17/320016
606/167
5,501,698 A * 3/1996 Roth .................. A61B 17/1285
606/174

(Continued)

FOREIGN PATENT DOCUMENTS

CN   102817032 A * 12/2012 ............... C23C 8/80
CN   106319161 A    1/2017

(Continued)

OTHER PUBLICATIONS

International Search Report issued in PCT/JP2019/026112 dated Aug. 13, 2019 with English Translation (5 pages).

(Continued)

*Primary Examiner* — Katherine M Shi
(74) *Attorney, Agent, or Firm* — J-Pat U.S. Patent Legal Services; James Judge

(57) ABSTRACT

A medical instrument with excellent operability is provided. The medical instrument includes stick-shaped extra-narrow metal members. The extra-narrow member has a hardened layer formed on the surface thereof without losing flexibility.

6 Claims, 8 Drawing Sheets

(51) Int. Cl.
*A61B 17/3201* (2006.01)
*C23C 8/22* (2006.01)
*C23C 8/26* (2006.01)
*C23C 8/34* (2006.01)
*A61B 17/00* (2006.01)

(52) U.S. Cl.
CPC .............. *C23C 8/26* (2013.01); *C23C 8/34* (2013.01); *A61B 2017/00526* (2013.01); *A61B 2217/005* (2013.01)

(58) Field of Classification Search
CPC .... A61B 2017/00526; A61B 2017/305; A61B 2017/320072; A61B 2017/2217; A61B 2017/005; C23C 8/22; C23C 8/26; C23C 8/34; C23C 8/36; C23C 8/20; C23C 8/24; C23C 8/30; C23C 8/32; C23C 8/38
USPC ......................................................... 606/170
See application file for complete search history.

(56) References Cited

U.S. PATENT DOCUMENTS

| | | | | |
|---|---|---|---|---|
| 6,139,560 | A * | 10/2000 | Kremer | A61F 9/013 606/107 |
| 6,908,476 | B2 * | 6/2005 | Jud | A61B 17/320016 606/107 |
| 8,585,735 | B2 * | 11/2013 | Nallakrishnan | A61B 17/29 606/205 |
| 9,381,111 | B2 * | 7/2016 | Hickingbotham | A61M 37/0069 |
| 10,588,652 | B2 * | 3/2020 | Scheller | A61F 9/007 |
| 11,160,935 | B2 * | 11/2021 | Scheller | A61B 17/2909 |
| 2001/0056286 | A1 * | 12/2001 | Etter | A61B 17/2909 606/205 |
| 2005/0221072 | A1 * | 10/2005 | Dubrow | A61K 47/6957 428/292.1 |
| 2006/0058843 | A1 * | 3/2006 | Mashiko | A61C 5/42 606/222 |
| 2008/0099108 | A1 | 5/2008 | Baudis et al. | |
| 2008/0188877 | A1 * | 8/2008 | Hickingbotham | A61B 17/3211 606/162 |
| 2012/0150216 | A1 * | 6/2012 | Hickingbotham | A61B 17/30 606/206 |
| 2013/0108886 | A1 * | 5/2013 | Jahrling | C23C 4/129 428/601 |
| 2015/0088193 | A1 * | 3/2015 | Scheller | A61B 17/30 606/207 |
| 2016/0262931 | A1 * | 9/2016 | Bhattacharjee | A61F 9/007 |
| 2016/0287320 | A1 * | 10/2016 | Hiller | A61B 18/1447 |
| 2017/0189045 | A1 * | 7/2017 | Scheller | A61B 17/30 |
| 2018/0133056 | A1 * | 5/2018 | Kahook | A61F 9/00736 |
| 2021/0093480 | A1 * | 4/2021 | Tazawa | A61F 9/00736 |

FOREIGN PATENT DOCUMENTS

| | | | | |
|---|---|---|---|---|
| JP | 2006-77313 A | 3/2006 | | |
| JP | 2007-332459 A | 12/2007 | | |
| JP | 2016-500297 A | 1/2016 | | |
| WO | WO-9822024 A1 * | 5/1998 | ............ | A61M 25/09 |
| WO | WO-2014092956 A1 * | 6/2014 | ............ | A61B 17/282 |
| WO | WO-2017005488 A1 * | 1/2017 | ............ | A61L 31/022 |

OTHER PUBLICATIONS

Extended European Search Report issued in European Patent Application No. 19827376.5, dated Feb. 25, 2022 (10 pages), 10 pages.
Sun Yong: "The response of austenitic stainless steels to low-temperature plasma nitriding", Heat Treatment of Metals, vol. 26, No. 1, Jan. 1, 1999, pp. 9-16, XP055892006 (9 pages).
Meletis E I et al.: "On the Single Phase Formed During Low-Temperature Plasma Nitriding of Austenitic Stainless Steels", Journal of Materials Science Letters, Chapman and Hall Ltd, London, GB, vol. 21, No. 15, Aug. 1, 2002, pp. 1171-1174, XP001125569, ISSN: 0261-8028 (4 pages).
Liu Ran et al.: "Surface modification of a medical grade Co—Cr—Mo alloy by low temperature plasma surface alloying with nitrogen and carbon", Surface and Coatings Technology, vol. 232, Oct. 15, 2013, pp. 906-911, XP028707169, ISSN: 0257-8972 (6 pages).

* cited by examiner

MEDICAL INSTRUMENT, MEDICAL DEVICE, METHOD OF MANUFACTURING MEDICAL INSTRUMENT, AND METAL ARTICLE

TECHNICAL FIELD

The present disclosure relates to a medical instrument etc. provided with an extra-narrow metal member.

BACKGROUND ART

Conventionally, in a medical site, medical instruments provided with an extra-narrow metal member (e.g., ocular forceps, ocular cutter, etc.) are used. For example, Patent Document 1 discloses membrane forceps for treating an ocular symptom.

In detail, the membrane forceps disclosed in Patent Document 1 include a handle, a probe actuation handle, a probe actuation tube, and forceps jaws (probe tip end). The tube is any appropriate medical-grade tube made of titanium, stainless steel, suitable polymer, etc. and is sized so that the forceps jaws can easily reciprocate inside the tube. The forceps jaws are generally made of stainless steel or titanium.

REFERENCE DOCUMENT OF CONVENTIONAL ART

Patent Document

[Patent Document 1] JP2016-500297A

DESCRIPTION OF THE DISCLOSURE

Problem to be Solved by the Disclosure

In the conventional medical instrument provided with the extra-narrow metal member, just a little force applied on the extra-narrow member causes a comparatively large deflection of the extra-narrow member. Thus, in use of the medical instrument, just a little contact of the extra-narrow member with a human tissue etc. causes the comparatively large deflection of the extra-narrow member, which makes the operation difficult for a user. Therefore, expert skill is required for appropriately operating the conventional medical instrument.

The present disclosure is made in view of the above situation, and one purpose thereof is to provide a medical instrument etc. with excellent operability, which improves deflection resistance of the extra-narrow member, while keeping its flexibility.

SUMMARY OF THE DISCLOSURE

In order to solve the above problem, according to the first aspect of the present disclosure, a medical instrument is provided, which includes a stick-shaped extra-narrow metal member. The extra-narrow member has a hardened layer formed on the surface thereof without losing flexibility.

According to the second aspect of the present disclosure, in the first aspect, the hardened layer may have a thickness of 2 μm or more and 18 μm or less.

According to the third aspect of the present disclosure, in the first or second aspect, the extra-narrow member may have a thickness of 1 mm or less.

According to the fourth aspect of the present disclosure, in any one of the first to third aspects, the hardened layer may be comprised of an S-phase formed by nitriding or carburizing.

According to the fifth aspect of the present disclosure, in any one of the first to fourth aspects, the hardened layer may be comprised of an S-phase formed by nitriding and carburizing in combination.

According to the sixth aspect of the present disclosure, in any one of the first to fifth aspects, the medical instrument may be ocular forceps including a tubular shaft, a stick-shaped core inserted inside the shaft, and a tip-end part openably and closably provided at a tip-end side of the core so as to be exposed outside the shaft. The shaft may correspond to the extra-narrow member and have the hardened layer formed on the surface thereof, without losing the flexibility.

According to the seventh aspect of the present disclosure, in any one of the first to fifth aspects, the medical instrument may be an ocular cutter including a tubular shaft provided with a blade and a suction port at a tip-end part thereof. The shaft may correspond to the extra-narrow member and have the hardened layer formed on the surface thereof, without losing the flexibility.

According to the eighth aspect of the present disclosure, a medical device is provided, which includes the medical instrument of the sixth or seventh aspect, and a handle to which the medical instrument is attached.

According to the ninth aspect of the present disclosure, a method of manufacturing a medical instrument including a stick-shaped extra-narrow metal member is provided. The method includes the step of forming a hardened layer on the surface of the extra-narrow member under a given condition where the extra-narrow member does not lose flexibility.

According to the tenth aspect of the present disclosure, a metal article is provided, which includes a stick-shaped or linear extra-narrow metal member with a thickness of 1 mm or less. The extra-narrow member has a hardened layer formed on the surface thereof without losing flexibility.

According to the eleventh aspect of the present disclosure, a metal article is provided, which includes an extra-thin metal member with a thickness of 1 mm or less. The extra-thin member has a hardened layer formed on the surface thereof without losing flexibility.

According to the twelfth aspect of the present disclosure, a metal article is provided, which includes a minute metal member with a maximum size of 1 mm or less in the length and the width. The minute member has a hardened layer formed on the surface thereof.

Effect of the Disclosure

According to the present disclosure, the extra-narrow member has the hardened layer formed on the surface thereof without losing flexibility. Since the extra-narrow member after the formation of the hardened layer has flexibility, it is unlikely to be cracked even when bent to an ordinary extent, and also has increased deflection resistance as a result of the formation of the hardened layer. Therefore, the present disclosure provides the medical instrument with excellent operability, which can prevent such a case that just a little contact of the extra-narrow member with a human tissue etc. in use of the medical instrument causes the comparatively large deflection.

MODE FOR CARRYING OUT THE DISCLOSURE

Hereinafter, one embodiment of the present disclosure is described in detail with reference to FIGS. 1-14. Note that the embodiment below is one example of the present disclosure, and is not intended to limit the scope of the present disclosure, articles to which the present disclosure is applicable, or a use of the present disclosure.

Figure 1:
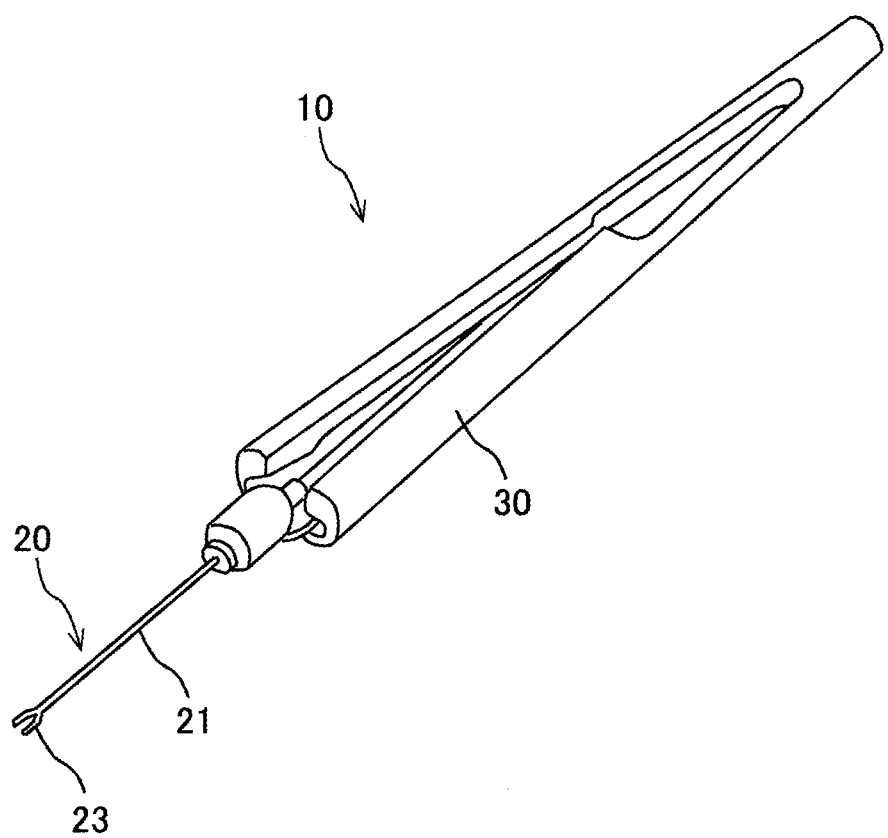
FIG. 1 is a perspective view of an ophthalmic medical device according to one embodiment.

This embodiment relates to a medical instrument 20 provided with a stick-shaped extra-narrow member 21 which is made of metal. The medical instrument 20 is a component of a medical device 10. In the medical instrument 20, for example, the extra-narrow member 21 does not have a needle at tip end or the extra-narrow member 21 does not have blade portion. The medical device 10 illustrated in FIG. 1 is an ophthalmic medical device used in retina and vitreous surgery, and is provided with ocular forceps 20 as the medical instrument 20 described above. Note that the extra-narrow member 21 has a thickness of 1 mm or less (particularly 0.5 mm or less).

[Configuration of Ophthalmic Medical Device]

As illustrated in FIG. 1, the ophthalmic medical device 10 is provided with the ocular forceps 20 described above, and a handle 30 used for opening and closing the ocular forceps 20. The ocular forceps 20 is removably attached to a tip-end part of the handle 30. The handle 30 is openable and closable, with its rear-end part (upper right part in FIG. 1) as a fulcrum. When a user opens or closes the handle 30, a converting mechanism (not illustrated) built in the handle 30 converts the opening or closing motion of the handle 30 into an axial motion of a core 22 (described later) of the ocular forceps 20, so that the core 22 reciprocates along the axial direction. In the ocular forceps 20, a tip-end part 23 opens or closes as the core 22 reciprocates.

[Configuration of Ocular Forceps]

Figure 2:
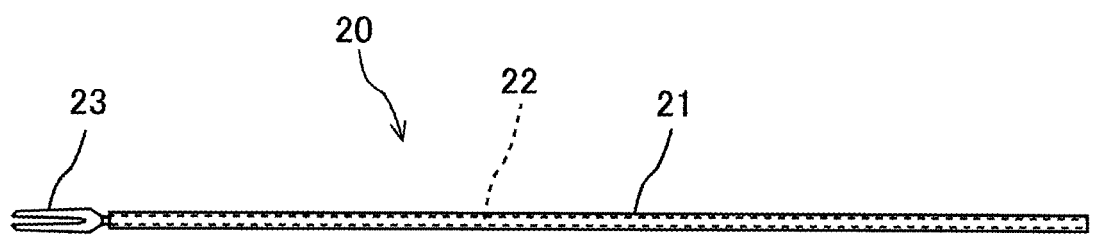
FIG. 2 is a plan view of ocular forceps.

As illustrated in FIG. 2, the ocular forceps 20 is provided with a tubular shaft 21, the core 22 which has a stick-like shape and is inserted inside the shaft 21, and the tip-end part 23 which is openably and closably provided at the tip-end side of the core 22 so as to be exposed outside the shaft 21.

The tip-end part 23 is comprised of scissors for cutting an object, or a gripping part for gripping an object.

The shaft 21 is a straight, circular tubular member. Meanwhile, the core 22 is a straight member with a circular cross section. The core 22 has a length slightly larger than that of the shaft 21, and has a thickness (outer diameter) slightly smaller than the inner diameter of the shaft 21. The tip-end side of the core 22 is integrated with the tip-end part 23. The core 22 is covered by the shaft 21, except the both end parts.

Regarding a material of the ocular forceps 20, the members of the ocular forceps 20 (i.e., the shaft 21, the core 22, and the tip-end part 23) are made of austenitic stainless steel, such as SUS304 and SUS316. SUS304 (JIS, corresponding to ISO No. 304) is an austenitic stainless steel having a chemical component composition containing, by mass, 18-20% Cr, 8-10.5% Ni, 0.08% or less C, 1% or less Si, 2% or less Mn, 0.045% or less P, and 0.03% or less S. SUS316 (JIS, corresponding to ISO No. 316) is an austenitic stainless steel having a chemical component composition containing, by mass, 16-18% Cr, 10-14% Ni, 2-3% Mo, 0.08% or less C, 1% or less Si, 2% or less Mn, 0.045% or less P, and 0.03% or less S.

Note that the austenitic stainless steel used for the members of the ocular forceps 20 is a stainless steel in which a single phase of austenite is formed in an ordinary temperature range, and in addition to the SUS304 and SUS316 described above, SUS201 (JIS), SUS202 (JIS), SUS301 (JIS), SUS303 (JIS), SUS305 (JIS), and SUS317 (JIS) may be used.

Moreover, in addition to the austenitic stainless steels, examples of the material of the ocular forceps 20 may include stainless steels of other steel type, cobalt-chromium-nickel alloys, nickel-chromium alloys, cobalt-chromium alloys, aluminum alloys, titanium, magnesium, etc.

The ocular forceps 20 is, for example, forceps with a thickness of 27 Gauge (0.41±0.02 mm). The shaft 21 has a length of 30 mm, an outer diameter of 0.41 mm, and an inner diameter of 0.2 mm. Moreover, the core 22 has a length of 35 mm and a thickness of 0.15 mm Both the shaft 21 and the core 22 correspond to the extra-narrow metal member with a stick-like shape. In the ocular forceps 20, a base of each of the shaft 21 and the core 22 is fixed or coupled to the handle 30. Thus, if force is applied to the tip-end part of the shaft 21, for example, deflection is caused. Note that the size of the ocular forceps 20 is not limited to the values described in this paragraph.

Figure 3:
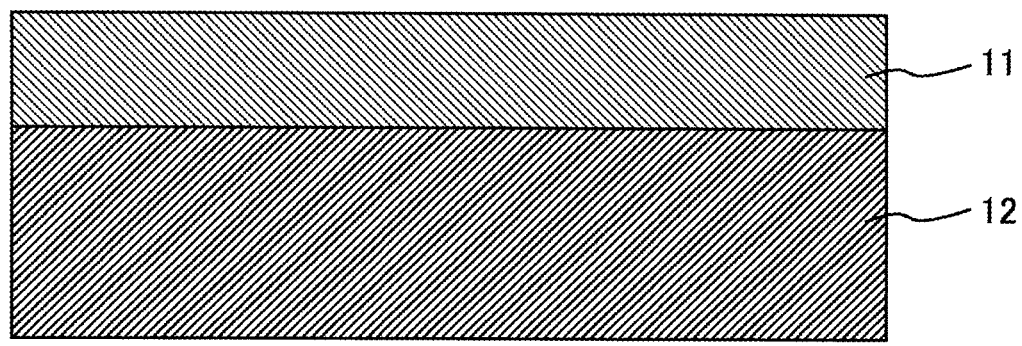
FIG. 3 is a cross-sectional view of a surface part of the ocular forceps.

In this embodiment, in order to increase the resistance to such deflection, the shaft 21 has on its surface a hardened layer 11 formed by a plasma nitriding treatment. As illustrated in FIG. 3, a surface of a base material 12 of the ocular forceps 20 is covered by the hardened layer 11. As a method of forming the hardened layer 11, other nitriding treatments (e.g., gas nitriding and salt bath nitriding) may also be employed. Moreover, the hardened layer 11 may be formed by a carburizing treatment. As a method of the carburizing treatment, any of plasma carburizing, gas carburizing, and salt bath carburizing may be employed. Moreover, the nitriding treatment and the carburizing treatment may be employed in combination. In such a case, the two treatments may be performed serially. Alternatively, a carbonitriding treatment in which the two treatments are performed at the same time may be employed. Herein, the term "surface heat treatment" is used as a generic term including the nitriding treatment, the carburizing treatment, and the carbonitriding treatment. Moreover, PVD (physical vapor deposition) may be employed to form the hardened layer 11 (diamond-like carbon thin film etc.). Moreover, the surface may be coated or plated.

Here, the surface heat treatment such as the nitriding treatment and the carburizing treatment is used for enhancing the abrasion resistance of the member made of metal such as stainless steel. In order to enhance the abrasion resistance, it is necessary to form a thick hardened layer. In the surface heat treatment, as a surface temperature (treatment temperature) of a material to be treated during the surface treatment is increased, the treatment period until formation of a thick hardened layer becomes shorter. Thus, a high treatment temperature of 500° C. or higher is employed. However, when performing the surface heat treatment on the extra-narrow shaft 21 under treatment conditions (e.g., treatment temperature) where a thick hardened layer is obtained, if a ratio of the thickness of the hardened layer 11 to the entire thickness of the shaft 21 becomes high, the shaft 21 loses the flexibility. In such a case, the shaft 21 is cracked when a user tries to bend it.

On the other hand, in this embodiment, the surface heat treatment is performed on the shaft 21 under treatment conditions where the thin hardened layer 11 is obtained. The thickness of the hardened layer 11 in the shaft 21 (extra-narrow member) may be, for example, 2 μm or more, and may be 4 μm or more. Moreover, the thickness of the hardened layer 11 may be 18 μm or less, and may be 15 μm or less, or 10 μm or less. For example, the thickness of the hardened layer 11 is 2 μm or more and 18 μm or less (preferably 2 μm or more and 15 μm or less, more preferably 4 μm or more and 10 μm or less). Moreover, the ratio of the cross-sectional area of the hardened layer 11 to the entire cross-sectional area of the shaft 21 (extra-narrow member) is, for example, 2% or more and 20% or less (preferably 5% or more and 12% or less, more preferably 5% or more and 10% or less). According to this embodiment, the shaft 21 with higher deflection resistance than an untreated (i.e., not surface heat treated) material can be achieved without losing the flexibility of the shaft 21. The shaft 21 has improved elasticity. Note that the thickness of the hardened layer 11 formed by the nitriding, carburizing, or carbonitriding treatment refers to a thickness with which the element (nitrogen or carbon) contained in the treated material can be observed in thickness measurement using glow discharge spectrometer (described later).

Regarding the elasticity of the 27-Gauge shaft 21, if it is made of stainless steel, a compressive load measured when an amount of downward deflection at the center is 3 mm in the three-point bending test (1) (described later) is 0.5N or more and 1.0N or less, preferably 0.7N or more (a compressive load of the untreated material is about 0.3N). Moreover, if the shaft 21 is made of cobalt-chromium-nickel alloy, the compressive load measured when the amount of downward deflection at the center is 3 mm in the three-point bending test (1) is 1.1N or more and 1.3N or less. Details of the three-point bending test will be described in Examples.

Note that in this embodiment the hardened layer 11 is formed not only on the surface of the shaft 21 but also on the surface of the core 22, by the surface heat treatment (e.g., plasma nitriding treatment and plasma carburizing treatment) etc. However, for example, the hardened layer 11 may be formed only on the shaft 21 or only on the core 22, as long as it can achieve the ocular forceps 20 with the higher elasticity than with the untreated material. Moreover, although in this embodiment the hardened layer 11 is formed on the entire outer surface of both the shaft 21 and the core 22, their outer surfaces may include an area in which the hardened layer 11 is not formed, as long as it can achieve the ocular forceps 20 with the higher elasticity than with the untreated material.

Moreover, as the performance other than that measured in the three-point bending test, the shaft 21 made of SUS304 or SUS316 which has been nitrided at a temperature within a given range has an indentation hardness (surface hardness) of $15,000 N/mm^2$ or more at an indentation load of 10 mN, as determined by a nanoindentation test according to ISO 14577-1:2002, and a corrosion resistance of a level in which substantially no rust occurs in appearance even after carrying out a neutral salt spray test for corrosion resistance according to JIS Z2371:2015 (ISO 9227:2012) for 150 hours. Meanwhile, the shaft 21 made of SUS304 or SUS316 which has been carburized at a temperature within a given range has an indentation hardness of $12,000 N/mm^2$ or more at an indentation load of 10 mN, as determined by the nanoindentation test according to ISO 14577-1:2002, and a corrosion resistance of a level in which substantially no rust occurs in appearance even after carrying out the neutral salt spray test for corrosion resistance according to JIS Z2371: 2015 (ISO 9227:2012) for 150 hours.

[Method of Manufacturing Medical Instrument]

A method of manufacturing the medical instrument 10 according to one embodiment will be described. In particular, a method of the surface heat treatment is described in detail.

In this manufacturing method, first, metal processing is performed to prepare the shaft 21 and the core 22 as the to-be-treated materials. The core 22 is prepared as integrated with the tip-end part 23. Next, the surface heat treatment, such as the nitriding treatment, the carburizing treatment, the heat treatment in which the nitriding and carburizing treatments are performed serially, or the carbonitriding treatment, is performed on each of the shaft 21 and the core 22 under given treatment conditions (e.g., treatment temperature and treatment period) where their flexibility is not lost, to form on their surface the hardened layer 11. Next, each of the treated materials 21 and 22 is cooled, and then the core 22 is set in the shaft 21 to complete the ocular forceps 20.

As one example of the formation of the hardened layer, the plasma nitriding treatment is described. In this case, first, the to-be-treated materials 21 and 22 are placed in a treatment chamber of a vacuum furnace of a plasma treatment apparatus, and the treatment chamber is sealed. Gas inside the treatment chamber is exhausted by a pump to make the treatment chamber in a vacuum state (e.g., medium vacuum state), and then mixture gas of hydrogen and nitrogen is introduced into the treatment chamber to generate glow discharge between a positive electrode (inner wall of the vacuum furnace) and a negative electrode (the to-be-treated materials 21 and 22).

During a glow-discharge generation period, the surface temperature of the to-be-treated materials 21 and 22 is measured by, for example, a thermometer (e.g., radiation thermometer, thermocouple, etc.). During the glow-discharge generation period, the surface temperature of the to-be-treated materials 21 and 22 gradually increases, and a nitrided layer starts to be formed on their surface. When the surface temperature of the to-be-treated materials 21 and 22 further increases to reach a set temperature (treatment temperature) set at the plasma treatment apparatus, the surface temperature of the to-be-treated materials 21 and 22 is maintained at the set temperature. The plasma treatment apparatus performs a feedback control of voltage and current values between the positive and negative electrodes so as to maintain the measurement of the thermometer, for example, at the set temperature. In the plasma treatment apparatus, the glow discharge is continued until the set time (treatment period) set for the plasma treatment apparatus is elapsed. Thus, the formation of the hardened layer is ended.

Among the treatment conditions of the surface heat treatment, the treatment temperature (the surface temperature of the to-be-treated material during the surface heat treatment) can be adjusted in a temperature range where an expanded austenite phase (hereinafter, referred to as "S-phase") is formed on the surface of the to-be-treated materials 21 and 22, if the austenitic stainless steel is used as the to-be-treated materials 21 and 22. The S-phase means, in the case of the nitriding treatment, a supersaturated solid solution of nitrogen (carbon in the case of the carburizing treatment) having a face-centered cubic structure (FCC structure) with a lattice spacing larger than that of a normal austenite phase. In the case of the nitriding treatment, the hardened layer 11 is comprised of the S-phase formed by nitriding. In the case of the carburizing treatment, the hardened layer 11 is comprised of the S-phase formed by carburizing. In the case of the nitriding and carburizing treatments in combination (i.e., the carburizing treatment is performed after the nitriding treatment, the nitriding treatment is performed after the carburizing treatment, or the carbonitriding treatment is performed), the hardened layer 11 is comprised of the S-phase formed by the combination of the nitriding treatment and the carburizing treatment. In such a case, nitrogen atoms are present closer to the outer surface as compared to carbon atoms.

Regarding the temperature range in which the S-phase is formed, the treatment temperature of the nitriding treatment or the carbonitriding treatment is described in detail. If the steel type is SUS304, the treatment temperature is set 250° C. or higher and 430° C. or lower, preferably 300° C. or higher and 400° C. or lower, more preferably 340° C. or higher and 385° C. or lower. Moreover, if the steel type is SUS316, the treatment temperature is set 250° C. or higher and 450° C. or lower, preferably 350° C. or higher and 410° C. or lower, more preferably 360° C. or higher and 385° C. or lower.

Meanwhile, regarding the temperature range in which the S-phase is formed, the treatment temperature of the carburizing treatment is set, either the steel type is SUS304 or SUS316, 250° C. or higher and 450° C. or lower, preferably 340° C. or higher and 410° C. or lower, more preferably 350° C. or higher and 385° C. or lower.

Moreover, although the treatment period of the surface heat treatment can be appropriately set according to the required elasticity or thickness of the to-be-treated material, in the 27-Gauge ocular forceps 20, it is set 2 hours or more and 24 hours or less (preferably 2 hours or more and 10 hours or less, more preferably 2 hours or more and 6 hours or less), either the plasma nitriding treatment or the plasma carburizing treatment is employed, and either the steel type is SUS304 or SUS316.

Moreover, in the case of a cobalt-chromium-nickel alloy, if the nitriding treatment is performed, the treatment temperature is set 340° C. or higher and 600° C. or lower (e.g., 380° C.), and the treatment period is set to 1 hour or more and 4 hours or less, because they have excellent corrosion resistance. Note that, if the cobalt-chromium-nickel alloy is age-hardened and then subjected to the nitriding or carburizing treatment, the treatment temperature can be set 350° C. or higher and 420° C. or lower. The temperature at the time of the age hardening may be, for example, approximately 520° C. Moreover, if the cobalt-chromium-nickel alloy is subjected to the nitriding treatment or the carburizing treatment while being age-hardened, the treatment temperature can be set 450° C. or higher and 600° C. or lower.

If the treatment temperature is excessively low, or the treatment period is excessively short, it is not easy to give sufficient elasticity to the to-be-treated materials 21 and 22, and on the other hand, if the treatment temperature is excessively high or the treatment period is excessively long, the hardened layer 11 may be excessively thick to lose the flexibility.

Here, the austenitic stainless steel has a passive film formed on the surface and has excellent corrosion resistance, but if subjected to the surface heat treatment under treatment conditions which improves the abrasion resistance (in the case of the nitriding treatment, the treatment temperature of about 500-600° C.), the corrosion resistance is greatly reduced as compared to the untreated material. Moreover, in order to increase the corrosion resistance, the surface heat treatment at a low temperature of 400° C. has been attempted, which is disclosed in some documents (JP2015-048499A etc.) to achieve excellent corrosion resistance. However, in practice, it is common general technical knowledge among researchers and developers relevant to the surface heat treatment that even the surface heat treatment at a low temperature greatly reduces the corrosion resistance as compared to the untreated material. Further, the surface heat treatment is to be utilized for the purpose of improving the abrasion resistance, and the surface heat treatment at a low temperature has not been industrially utilized because its utility has not been found.

On the other hand, the present inventors considered that the surface heat treatment at a low temperature can be industrially utilized for the purpose of increasing the elasticity of the extra-narrow members 21 and 22. Then, by performing the surface heat treatment at a low temperature to form the hardened layer 11, which is a thin film, on the surface of the extra-narrow members 21 and 22, the present inventors successfully manufactured the medical instrument 20 which has increased elasticity and less tendency of deflection (i.e., a medical instrument with elasticity and less likely to be cracked) without losing the flexibility. The treatment temperature of this embodiment is in a temperature zone which is not used for improving the abrasion resistance. In this embodiment, a thin-film nitride layer 11 is formed by intentionally using the temperature zone in which the hardened layer 11 is slowly formed.

Moreover, regarding the treatment temperature when austenitic stainless steel is subjected to the surface heat treatment, the present inventors found that the hardened layer 11 (nitride layer or carburized layer) with corrosion resistance at equivalent or substantially equivalent level to that of untreated material (of the same steel type) can be obtained by setting the treatment temperature in a given temperature range lower than the conventionally attempted low temperature (400° C.). By the neutral salt spray test described later, the extremely excellent corrosion resistance was confirmed (see Tables 1 and 2 referred to later). The given temperature range is 340° C. or higher and 385° C. or lower, either the nitriding treatment or the carburizing treatment is employed, and either the steel type is SUS304 or SUS316.

Modification 1 of Embodiment

In this modification, the surface heat treatment, such as the plasma nitriding treatment, the plasma carburizing treatment, or the treatment in which the plasma nitriding treatment and the plasma carburizing treatment are performed in combination, is performed on the extra-narrow members 21 and 22 (such as the shaft 21) at the treatment temperature higher than the temperature range where the S-phase is formed, so that the hardened layer 11 is formed on the surface of the extra-narrow members 21 and 22.

The present inventors employed short treatment period in the formation of the hardened layer 11 on the surface of the extra-narrow members 21 and 22 by the surface heat treatment, so that the extra-narrow members 21 and 22 do not lose the flexibility even if the treatment temperature higher than the temperature range where the S-phase is formed is employed, and successfully manufactured the extra-narrow members 21 and 22 with high elasticity.

The treatment temperature of the nitriding treatment can be set 430° C. or higher and 600° C. or lower if the steel type is SUS304, and can be set 450° C. or higher and 600° C. or lower if the steel type is SUS316. Moreover, the treatment temperature of the carburizing treatment can be set 450° C. or higher and 600° C. or lower, either the steel type is SUS304 or SUS316. Further, the treatment period can be selected from values of 12 hours or less, and determined according to the required elasticity.

Modification 2 of Embodiment

In this modification, the plasma nitriding treatment and the plasma carburizing treatment are performed in combination on the extra-narrow members 21 and 22, to form the hardened layer 11 on the surface of the extra-narrow members 21 and 22. Regarding the order of performing the plasma nitriding treatment and the plasma carburizing treatment in this case, the plasma carburizing treatment may be performed after the plasma nitriding treatment, or the plasma nitriding treatment may be performed after the plasma carburizing treatment. Moreover, the plasma carbonitriding treatment may be performed, in which the two treatments are performed at the same time. Note that, when the plasma nitriding treatment and the plasma carburizing treatment are performed separately, the plasma nitriding treatment and the plasma carburizing treatment may be performed either at the same treatment temperature or at different temperatures. Moreover, the plasma nitriding treatment and the plasma carburizing treatment may be performed either for the same treatment period or for different treatment periods.

Here, the present inventors found that, the combination of the plasma nitriding treatment and the plasma carburizing treatment results in higher elasticity than the plasma nitriding treatment or the plasma carburizing treatment alone, when compared at the same treatment period. In this case, by performing the plasma nitriding treatment, the plasma carburizing treatment, or the plasma carbonitriding treatment in a temperature range where the S-phase is formed, the medical instrument 20 which has both the excellent corrosion resistance and the elasticity of the extra-narrow members 21 and 22 can be achieved.

Regarding the temperature range where the S-phase is formed, as described above, the treatment temperature of the nitriding treatment or the carbonitriding treatment is set, if the steel type is SUS304, 250° C. or higher and 430° C. or lower, preferably 300° C. or higher and 400° C. or lower, more preferably 340° C. or higher and 385° C. or lower. Moreover, if the steel type is SUS316, the treatment temperature is set 250° C. or higher and 450° C. or lower, preferably 350° C. or higher and 410° C. or lower, more preferably 360° C. or higher and 385° C. or lower. The treatment temperature of the carburizing temperature is set 250° C. or higher and 450° C. or lower, preferably 340° C. or higher and 410° C. or lower, more preferably 350° C. or higher and 385° C. or lower, either the steel type is SUS304 or SUS316.

EXAMPLES

Hereinafter, the present disclosure is described in detail based on Examples. Note that the present disclosure is not limited to these Examples.

[Three-Point Bending Test (1)]

For each of Examples 1 to 6 and Comparative Example 1 in which the shaft 21 of the 27G ocular forceps was used as a sample, a three-point bending test was performed. All the samples (shaft 21) are the same in size. The size of each sample was 30 mm in length, 0.41 mm in outer diameter, and 0.2 mm in inner diameter.

Figure 4:
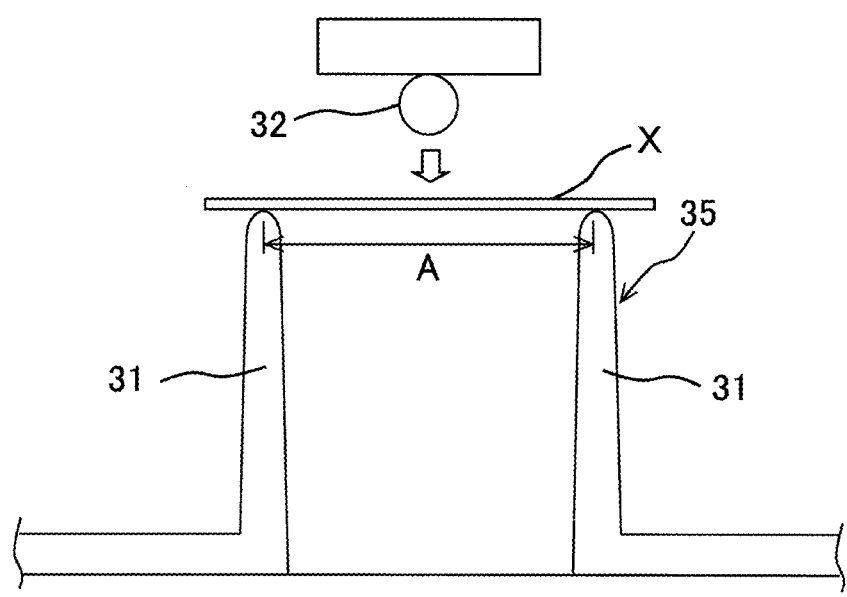
FIG. 4 is a schematic view for illustrating a method of three-point bending test.
Figure 5:
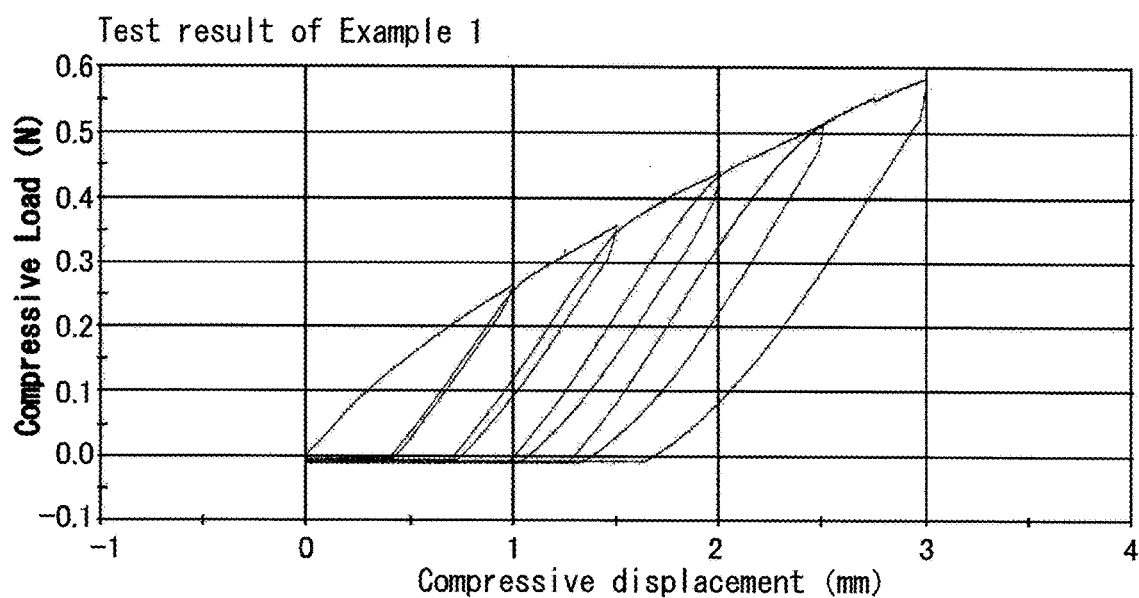
FIG. 5 is a chart illustrating results of the three-point bending test for Example 1.
Figure 6:
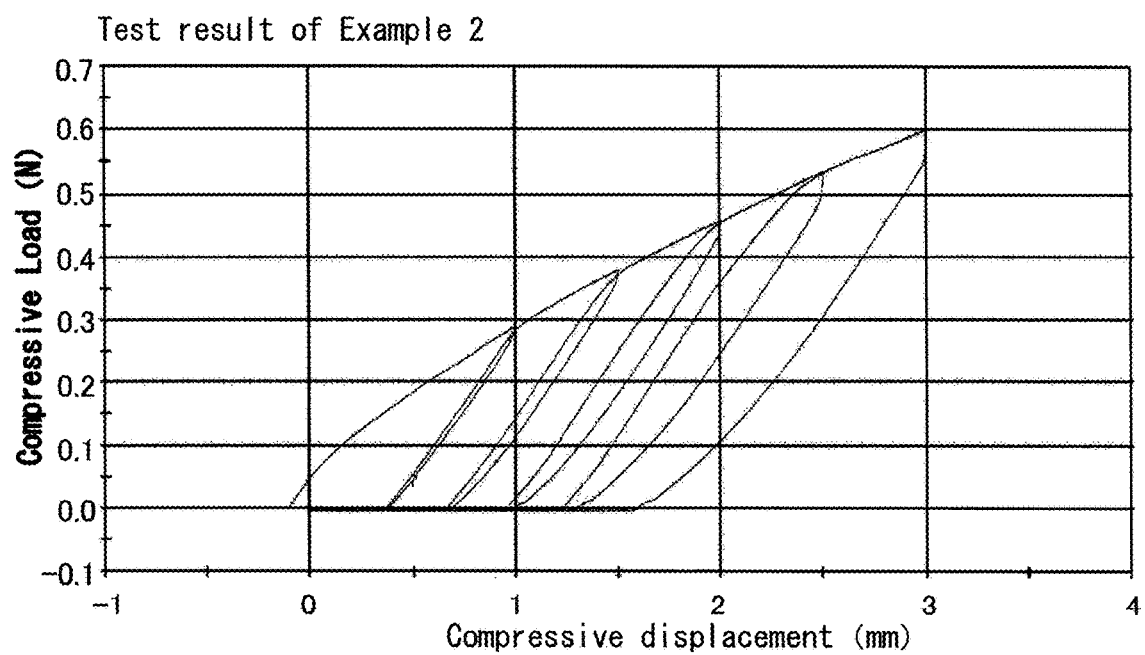
FIG. 6 is a chart illustrating results of the three-point bending test for Example 2.
Figure 7:
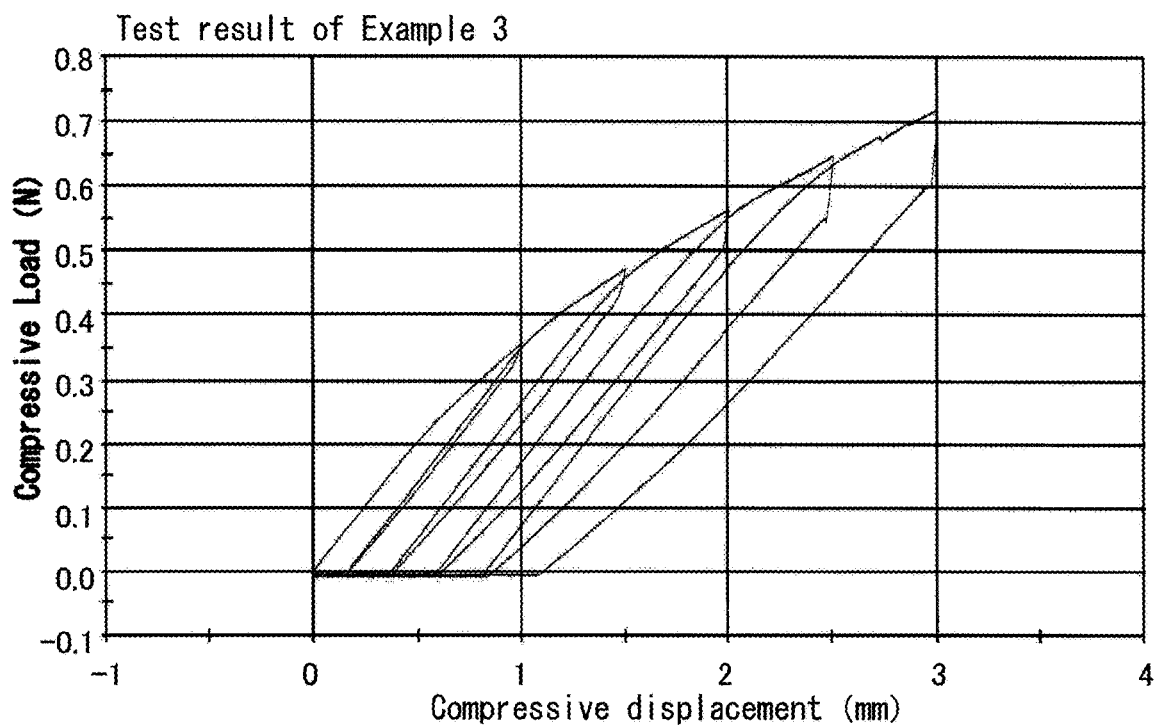
FIG. 7 is a chart illustrating results of the three-point bending test for Example 3.
Figure 8:
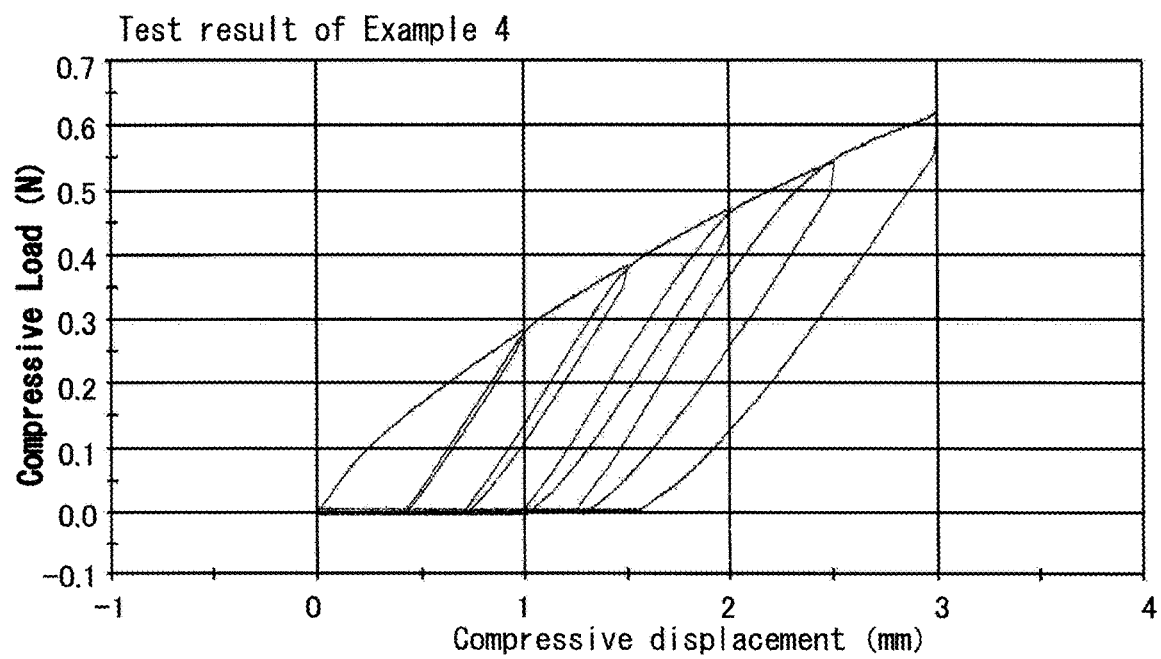
FIG. 8 is a chart illustrating results of the three-point bending test for Example 4.
Figure 9:
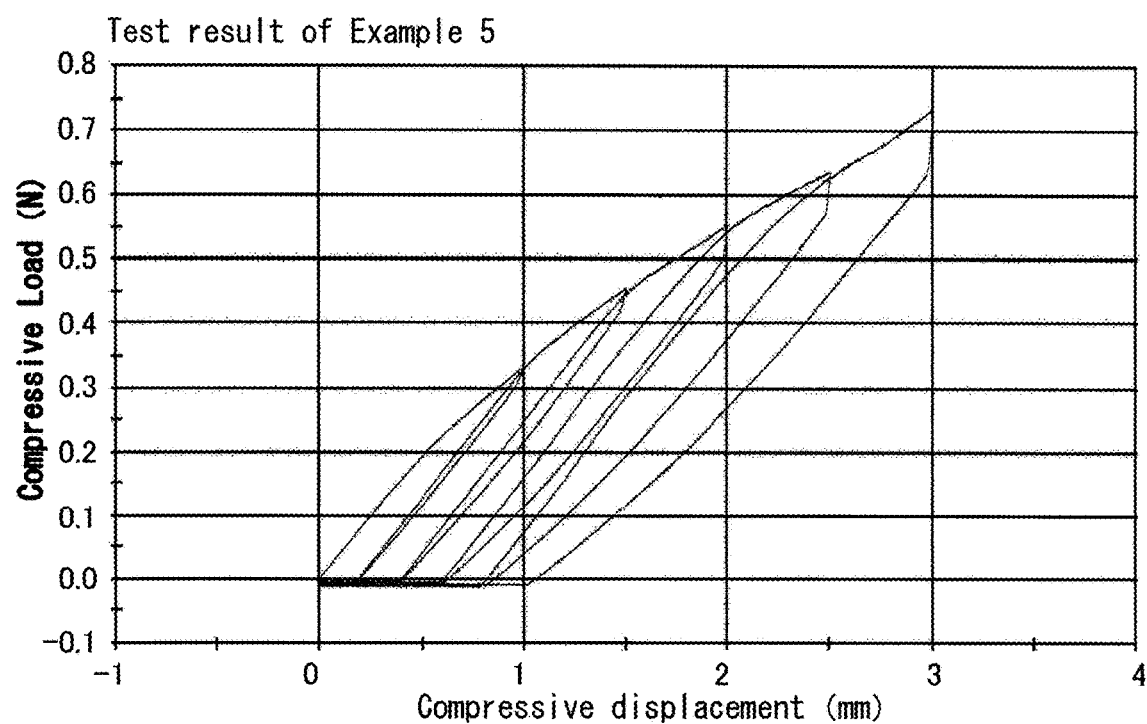
FIG. 9 is a chart illustrating results of the three-point bending test for Example 5.
Figure 10:
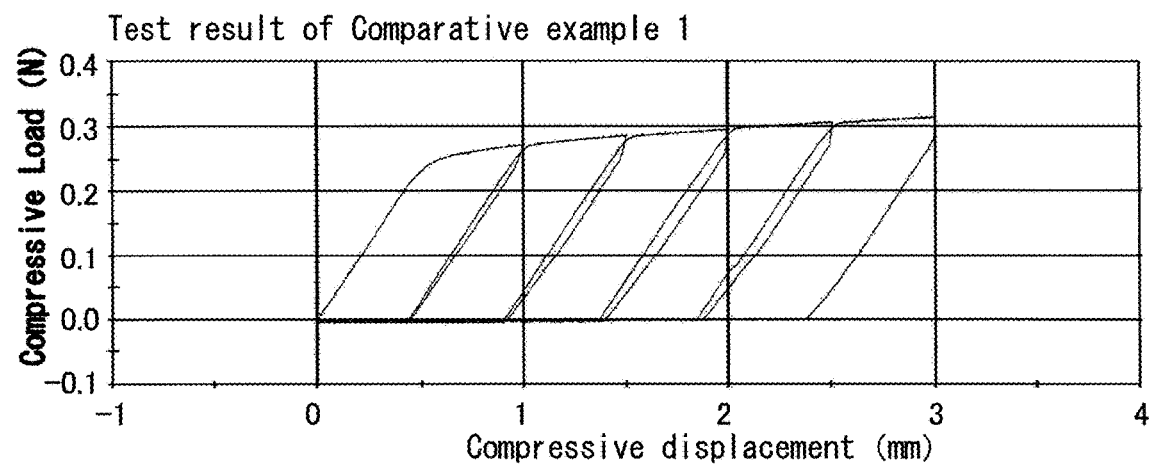
FIG. 10 is a chart illustrating results of the three-point bending test for Comparative Example 1.

For the three-point bending test, a jig 35 illustrated in FIG. 4 and the Instron 5569 universal material testing machine (available from Instron) were used. In the three-point bending test, as illustrated in FIG. 4, a sample X was placed on a pair of supporting parts 31 of the jig 35, so that the centers of the sample X and the supporting parts were aligned. Then, using the Instron 5569 universal material testing machine, with a circular-cross-sectional rod member 32 attached orthogonally to the sample X, the rod member 32 was moved downward to indent the sample X from upward, and a load (compressive load) at which an amount of deflection of the sample X on the center thereof became a given value, was measured. In the three-point bending test, the compressive load was measured in a range in which the amount of deflection of the sample X on the center thereof was 1 mm to 3 mm, at a pitch of 0.5 mm A distance A between fulcrums supporting the sample X was 30 mm Note that the room temperature during the test was 20° C.±0.5° C.

For Examples 1-5 and Comparative Example 1, the shaft 21 made of SUS304 (JIS) was used as the sample. For Example 6, the shaft 21 made of a cobalt-chromium-nickel alloy was used as the sample. For Examples 1-6, the plasma nitriding treatment was performed on the surface, under the treatment conditions shown in Table 1. Moreover, for Comparative Example 1, a raw (i.e., not plasma-nitrided) material was used.

The procedure of the plasma nitriding treatment performed on Examples 1-6 is described. First, each sample was placed in a vacuum furnace of a plasma treatment apparatus. Next, gas inside the vacuum furnace was exhausted by a pump to make the vacuum furnace in a vacuum state, then glow discharge is generated between a positive electrode (inner wall of the vacuum furnace) and a negative electrode (sample), and then mixture gas containing nitrogen and hydrogen was introduced into the vacuum furnace to perform the nitriding treatment on the surface of the sample. During the glow-discharge generation period, the surface temperature of the sample was measured by a radiation thermometer, and a feedback control was performed for a plasma generating part of the plasma treatment apparatus, so that the surface temperature of the sample reaches a set temperature of the plasma treatment apparatus and then is maintained at the set temperature. The plasma treatment apparatus was stopped when the runtime of the nitriding treatment reached a set time. In the plasma treatment apparatus, the treatment temperature and the treatment period indicated in Table 1 were used as the treatment temperature and the treatment period, respectively.

TABLE 1

| Material type | Example No | Treatment condition | | |
|---|---|---|---|---|
| | | Treatment method | Treatment temperature | Treatment period |
| SUS304 | Example 1 | Plasma nitriding treatment | 350° C. | 2 hours |
| | Example 2 | | | 4 hours |
| | Example 3 | | | 8 hours |
| | Example 4 | | 380° C. | 2 hours |
| | Example 5 | | | 8 hours |
| | Comparative Example 1 | Untreated | — | — |
| cobalt-chromium-nickel alloys | Example 6 | Plasma nitriding treatment | 520° C. | 2 hours |

Figure 11:
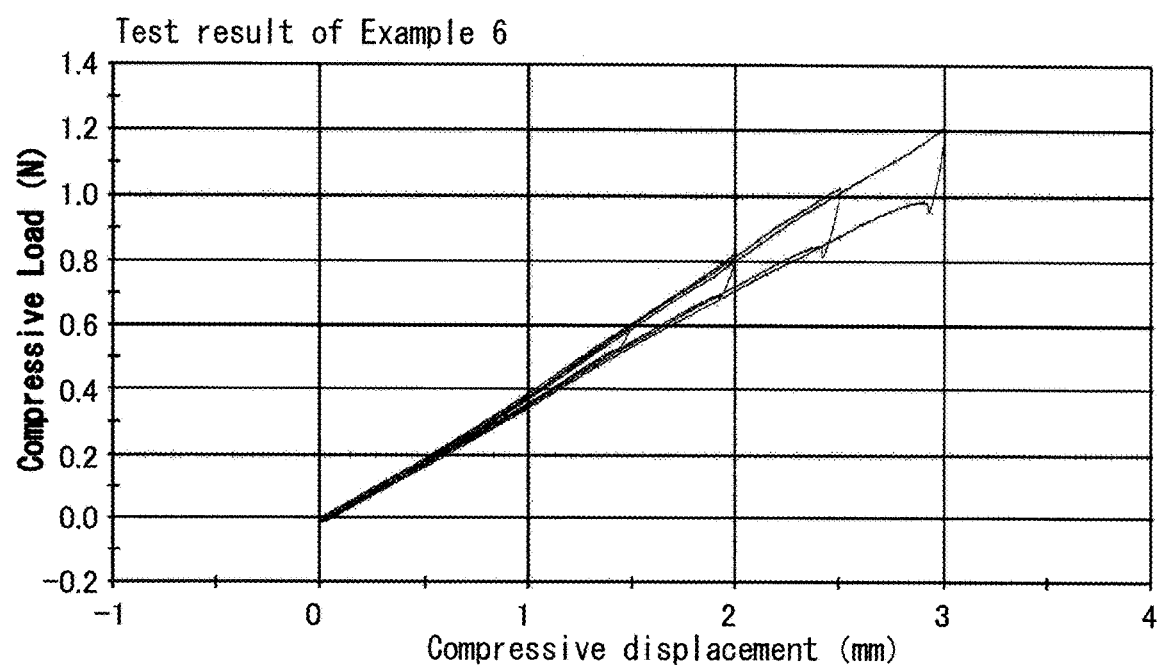
FIG. 11 is a chart illustrating results of the three-point bending test for Example 6.

Regarding test results for each of the Examples and the Comparative Example, as shown in FIGS. 5-10, when the material of the shaft 21 was SUS304, Examples 1-5 in which the hardened layer 11 was formed on the surface by the plasma nitriding treatment had a larger compressive load than that of Comparative Example 1, in which the hardened layer was not formed. Moreover, comparing Examples 1-3 in which the treatment temperature was 350° C., the compressive load increased as the treatment period increased. Similarly, also in Examples 4-5 in which the treatment temperature was 380° C., the compressive load increased as the treatment period increased. Moreover, as illustrated in FIG. 11, regarding the case where the material of the shaft 21 was the cobalt-chromium-nickel alloy, Example 6 in which the hardened layer 11 was formed by the plasma nitriding treatment had a large compressive load.

[Three-Point Bending Test (2)]

For Examples A-Q using the shaft 21 of the 27G ocular forceps as a sample, a three-point bending test was performed with a testing machine different from that used in the three-point bending test (1). For each of Examples A-Q, two or three samples were used. Note that each sample was the same in size as those used in the three-point bending test (1), and the material of each sample was SUS304 (JIS), same as in the three-point bending test (1).

As the testing machine for the three-point bending test, the force gauge ZTA-2N (available from Imada Co., Ltd.) was used. Moreover, in the three-point bending test, the sample X was placed on the pair of supporting parts 31 of the jig 35, so that the centers of the sample X and the supporting parts were aligned, as in the three-point bending test (1). Further, the circular-cross-sectional rod member 32 (FIG. 4) was attached to the testing machine (force gauge), and the testing machine was then attached to the vertical motorized test stand EMX-1000N (available from Imada Co., Ltd.), so that the rod member 32 was orthogonal to the sample X. Then, in the vertical motorized test stand, the testing machine with the rod member 32 was moved downward to indent the sample X from upward, and a load (compressive load) in which an amount of deflection (displacement) on its center became 1 mm, was measured by the testing machine. The distance A between the fulcrums supporting the sample X was 25 mm Note that the room temperature during the test was 20° C.±0.5° C.

The procedure of the plasma nitriding treatment was the same as in the Examples for the three-point bending test (1). Moreover, the procedure of the plasma carburizing treatment was the same as in the plasma nitriding treatment, except that mixture gas containing methane and hydrogen was introduced instead. For each Example, the test results are shown in Table 2, together with the treatment temperature, the treatment period, and the number of samples. As the test results, an average compressive load value (load value) of the plurality of samples, and a rate of increase of the compressive load relative to the average value of an untreated sample are indicated. Note that in Table 2 the circled numbers relevant to Examples N-Q represent the order of performing the plasma nitriding treatment and the plasma carburizing treatment.

TABLE 2

| Example No | Treatment condition | | | | Average Compressive Load | |
|---|---|---|---|---|---|---|
| | Treatment method | Treatment temperature | Treatment period | Number of samples | Load Value | Comparison with Untreated Sample |
| Example A | Plasma nitriding treatment | 300° C. | 2 hours | 2 | 0.493N | 105% |
| Example B | | 300° C. | 4 hours | 3 | 0.496N | 106% |
| Example C | | 360° C. | 2 hours | 3 | 0.498N | 106% |
| Example D | | 360° C. | 4 hours | 3 | 0.502N | 107% |
| Example E | | 360° C. | 20 hours | 2 | 0.51N | 109% |
| Example F | | 430° C. | 2 hours | 2 | 0.525N | 112% |
| Example G | | 520° C. | 1 hours | 3 | 0.576N | 123% |
| Example H | | 520° C. | 2 hours | 3 | 0.592N | 127% |
| Example I | Plasma carburizing treatment | 300° C. | 2 hours | 2 | 0.489N | 105% |
| Example J | | 300° C. | 4 hours | 2 | 0.49N | 105% |
| Example K | | 360° C. | 2 hours | 3 | 0.49N | 105% |
| Example L | | 520° C. | 2 hours | 3 | 0.514N | 110% |
| Example M | | 520° C. | 4 hours | 3 | 0.524N | 112% |
| Example N | ①Plasma nitriding treatment ②Plasma carburizing treatment | ①360° C. ②360° C. | ①2 hours ②2 hours | 3 | 0.526N | 113% |
| Example O | ①Plasma carburizing treatment ②Plasma nitriding treatment | ①300° C. ②300° C. | ①4 hours ②4 hours | 2 | 0.495N | 106% |
| Example P | | ①360° C. ②360° C. | ①2 hours ②2 hours | 2 | 0.528N | 113% |
| Example Q | | ①520° C. ②360° C. | ①4 hours ②2 hours | 3 | 0.532N | 114% |

According to the test results for the plasma-nitriding treatment, when compared at the same treatment period, the average compressive load value increased as the treatment temperature increased, and when compared at the same treatment temperature, the average compressive load value increased as the treatment period increased. Moreover, in the case of a treatment temperature (520° C.) higher than the temperature range in which the S-phase is formed (Examples G and H), the rate of increase relative to the untreated article was above 120%, and the rate of increase was considerably larger as compared with the case of a treatment temperature within the temperature range in which the S-phase is formed. This was more significant than in the case of the plasma carburizing treatment described later (Examples L and M). Moreover, according to the test results for the plasma carburizing treatment, when compared at the same treatment period, the average compressive load value increased as the treatment temperature increased, and when compared at the same treatment temperature, the average compressive load value increased as the treatment period increased.

Moreover, regarding the test results for the case where both the plasma nitriding treatment and the plasma carburizing treatment were performed, Examples N and P both showed the rate of increase of 113% relative to the untreated article, and had a larger rate of increase as compared with Example D with the same treatment temperature and the treatment period (total). It was found effective for enhancing the elasticity to perform both the plasma nitriding treatment and the plasma carburizing treatment.

[Corrosion Resistance Test]

For samples of SUS304 which underwent the surface heat treatment at a treatment temperature lower than 400° C. (Examples 7-8) and which underwent the surface heat treatment at a treatment temperature of 400° C. (Example 9), a corrosion resistance test was performed. For each sample, a stainless steel piece of 50 mm in length, 25 mm in width, and 5.0 mm in thickness was used. As a preparation step, each sample was subjected to six-sided milling, and on its front and back surfaces, plane grinding, wet paper polishing, and 3 μm diamond wrapping were further performed in this order. Next, the plasma nitriding treatment was then performed under the treatment conditions indicated in Table 3, in the same procedure as in the Examples for the three-point bending test.

Figure 12:
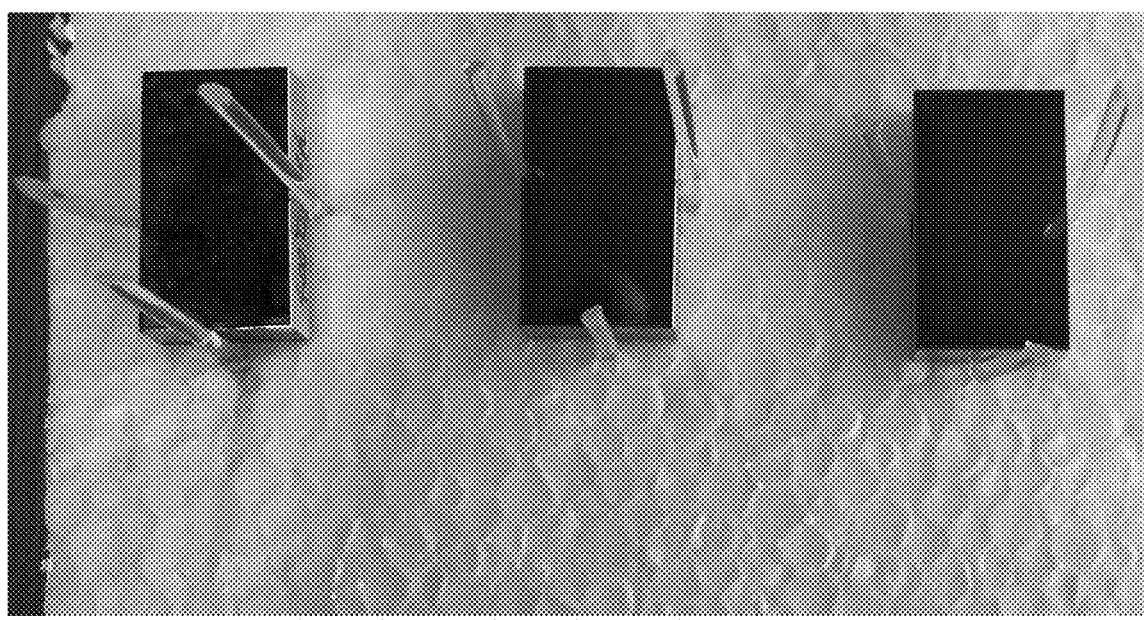
FIG. 12 illustrates a photograph of samples after a salt spray test for Examples 7-9, respectively.

As the corrosion resistance test, a neutral salt spray test was performed on each sample for one week, according to JIS Z2371:2015 (ISO 9227:2012). The test results are shown in Table 2. Moreover, a photograph of the samples after the salt spray test is illustrated in FIG. 12. In FIG. 12, the center is the photograph of Example 7, the right is the photograph of Example 8, and the left is the photograph of Example 9. As seen from Table 3 and FIG. 12, substantially no rusting was observed (neither was color change due to rusting) in any of the samples in Examples 7 and 8. On the other hand, in the sample of Example 9, rusting was observed significantly.

TABLE 3

| | | Example 7 | Example 8 | Example 9 |
|---|---|---|---|---|
| | | | Material type | |
| | | SUS304 | SUS304 | SUS304 |
| | | | Treatment method | |
| | | Nitriding treatment | Nitriding treatment | Nitriding treatment |
| Treatment condition | Treatment temperature | 350° C. | 370° C. | 400° C. |
| | Treatment period | 4 hours | 4 hours | 4 hours |
| Change in appearance | 4 hours later | No change | No change | Partialy turned blue-black |
| | 8 hours later | No change | No change | Partialy turned blue-black |
| | 1 day later (24 hours later) | No change | No change | Expansion of area with blue-black color change, and brown rust fluid dripping from the rear side of the specimen. |
| | 2 days later (48 hours later) | No change | No change | Same as one day later |
| | 3 days later (72 hours later) | No change | No change | Same as one day later |
| | 7 days later (168 hours later) | No change | No change | Same as one day later |

Moreover, in addition to the SUS304 samples indicated in Table 3, samples of the nitrided SUS316 (Examples 10-11), a sample of the carburized SUS304 (Example 12), and a sample of the carburized SUS316 (Example 13) were subjected for the neutral salt spray test described above for one week. The test results are shown in Table 4.

TABLE 4

| | | Example 10 | Example 11 | Example 12 | Example 13 |
|---|---|---|---|---|---|
| | | | Material type | | |
| | | SUS316 | | SUS304 | SUS316 |
| | | | Treatment method | | |
| | | Nitriding treatment | | Nitriding treatment | |
| Treatment condition | Treatment temperature | 350° C. | 380° C. | 380° C. | 380° C. |

TABLE 4-continued

| | | Example 10 | Example 11 | Example 12 | Example 13 |
|---|---|---|---|---|---|
| | | Material type | | | |
| | | SUS316 | | SUS304 | SUS316 |
| | | Treatment method | | | |
| | | Nitriding treatment | | Nitriding treatment | |
| | Treatment period | 4 hours | 4 hours | 4 hours | 4 hours |
| Change in appearance | 4 hours | No change | No change | No change | No change |
| | 1 day later | No change | No change | No change | No change |
| | 4 days later | No change | No change | No change | No change |
| | 7 days later | No change | No change | No change | No change |

In any of Examples 10-13, substantially no rusting was observed. According to Table 4, not only for the nitriding treatment of SUS304 but also for the nitriding treatment of SUS316 and the carburizing treatment of SUS304 and SUS316, it was confirmed that no rusting occurred even after the neutral salt spray test for 168 hours, in appearance of the stainless steel products with the treatment temperature of 385° C. or lower, even if the surface layer was not removed.

[Measurement of Thickness of Hardened Layer]

Samples (Examples 14-23) which underwent the surface heat treatment (plasma nitriding treatment or plasma carburizing treatment) under the treatment conditions indicated in Table 5 and in the same procedure as in the Examples for the three-point bending test were measured for the thickness of the hardened layer 11. In this measurement, using a glow discharge spectrometer (System 3860 available from Rigaku Corporation), a change in emission intensity of nitrogen in a depth direction was measured, and was converted into a concentration of nitrogen or carbon in the depth direction, by further using a calibration curve determining the correlation of the element concentration and the emission intensity.

TABLE 5

| | | | Treatment condition | |
|---|---|---|---|---|
| Material type | Example No | Treatment method | Treatment temperature | Treatment period |
| SUS304 | Example 14 | Plasma nitriding treatment | 350° C. | 4 hours |
| | Example 15 | | 380° C. | 4 hours |
| | Example 16 | | 400° C. | 4 hours |
| SUS316 | Example 17 | | 350° C. | 4 hours |
| | Example 18 | | 380° C. | 4 hours |
| | Example 19 | | 400° C. | 4 hours |
| SUS304 | Example 20 | Plasma carburizing treatment | 380° C. | 4 hours |
| | Example 21 | | 400° C. | 4 hours |
| SUS316 | Example 22 | | 380° C. | 4 hours |
| | Example 23 | | 400° C. | 4 hours |

Figure 13:
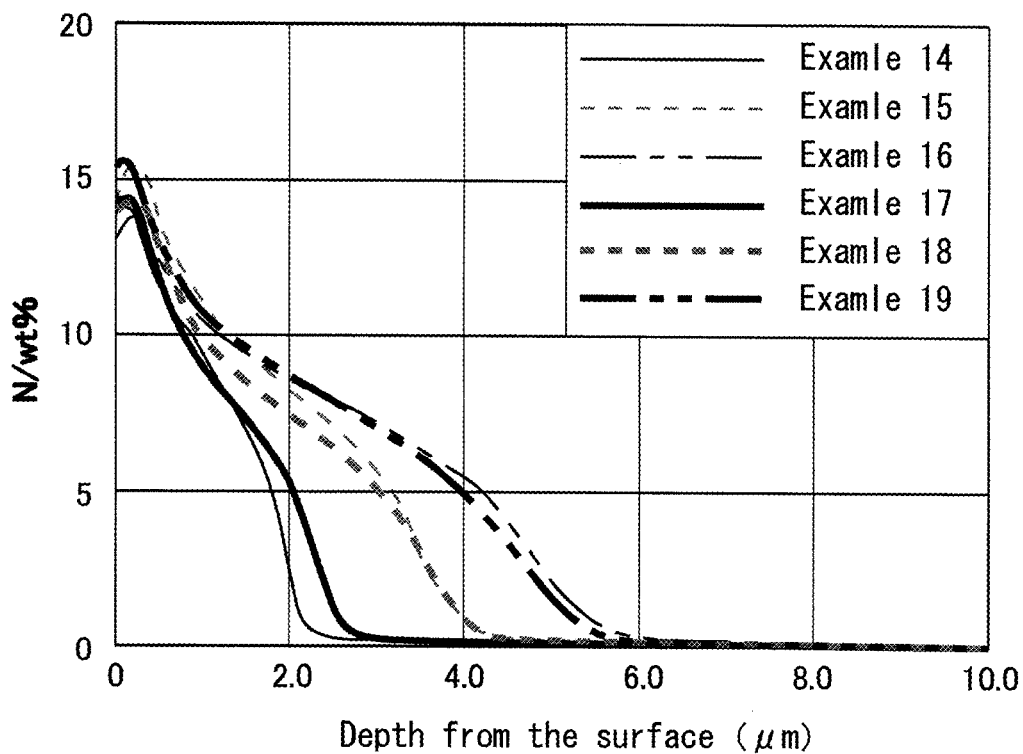
FIG. 13 is a chart illustrating nitrogen concentration profiles for plasma-nitrided samples (Examples 14-19).
Figure 14:
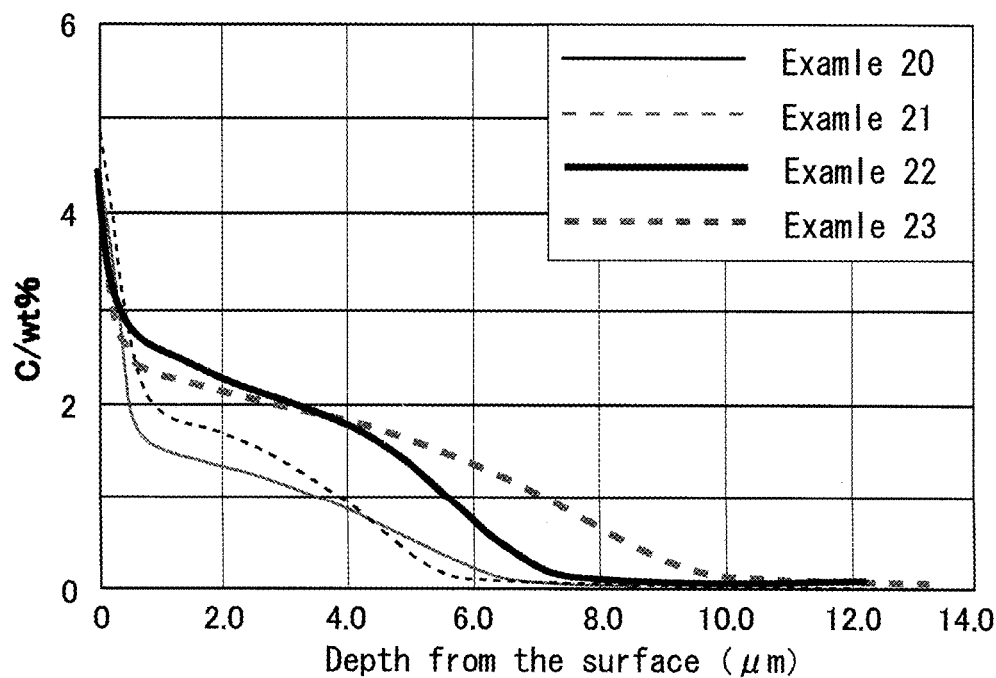
FIG. 14 is a chart illustrating carbon concentration profiles for plasma-carburized samples (Examples 20-23).

As test results, FIG. 13 illustrates the measurement results for the plasma-nitrided samples, and FIG. 14 illustrates the measurement results for the plasma-carburized samples. In FIG. 13, the thickness of the nitrided layer 11 was 2 μm to 6 μm. In Example 15 (with nitrided SUS304) in which the treatment temperature was 380° C. (the same treatment temperature as the sample which exhibited the compressive load of 0.6N or more and 0.75N or less), the thickness was 4 μm or more. Moreover, in FIG. 14, the thickness of the carburized layer 11 was 6 μm to 10 μm. Note that it is predicted that the hardened layer 11 becomes thicker than the thickness measurement results in FIGS. 13 and 14, if the treatment period is longer than 4 hours. Moreover, it is predicted that the thickness becomes greater if the plasma nitriding treatment and the plasma carburizing treatment are employed in combination, as compared to that in the case where either of these treatments is employed alone. It is predicted that the thickness of the hardened layer becomes up to about 18 μm.

[Measurement of Indentation Hardness by Nanoindentation Method]

For Examples 14-23, indentation hardness was measured by nanoindentaton method (nanoindentation hardness) according to ISO14577-1 (First edition, 2002 Oct. 1), by using a nanoindentation hardness tester available from ELIONIX, INC. (product name: ENT-1100a). For the measurement of each sample, the indentation load was set 10 mN. For each sample, measurement values were obtained at three or more points.

The test results are shown in Table 6. As the test results, the minimum, maximum, and average values for each sample are indicated. As used herein, the average value of the measurement results for the three or more points is referred to as "indentation hardness measured by nanoindentation method."

TABLE 6

| | | | Treatment condition | Indentation hardness (N/mm$^2$) | | |
|---|---|---|---|---|---|---|
| Material type | Example No | Treatment method | Treatment temperature | Maximum value | Minimum value | Average value |
| SUS304 | Example 14 | Plasma nitriding treatment | 350° C. | 20,150 | 15,530 | 17,576 |
| | Example 15 | | 380° C. | 17,190 | 13,920 | 15,820 |
| | Example 16 | | 400° C. | 18,370 | 13,210 | 16,783 |
| SUS316 | Example 17 | | 350° C. | 20,040 | 16,050 | 18,304 |
| | Example 18 | | 380° C. | 17,510 | 16,420 | 17,033 |
| | Example 19 | | 400° C. | 18,150 | 14,880 | 15,988 |

TABLE 6-continued

| Material type | Example No | Treatment method | Treatment condition Treatment temperature | Indentation hardness (N/mm$^2$) Maximum value | Minimum value | Average value |
|---|---|---|---|---|---|---|
| SUS304 | Example 20 | Plasma | 380° C. | 15,630 | 12,610 | 14,205 |
| | Example 21 | carburizing | 400° C. | 13,520 | 11,550 | 12,483 |
| SUS316 | Example 22 | treatment | 380° C. | 17,000 | 13,540 | 15,382 |
| | Example 23 | | 400° C. | 16,500 | 12,280 | 14,740 |

According to Table 6, in the case of the plasma-nitrided samples, the average value of the indentation hardness was 15,000 N/mm$^2$ or more. Moreover, in the case of the plasma-carburized samples, the average value of the indentation hardness was 12,000N/mm$^2$ or more.

[Applicability of the Present Disclosure]

The present disclosure is also applicable to a medical instrument 20 other than the ocular forceps 20, and may be applied to an ocular cutter including a tubular shaft which is provided with a blade and a suction port at a tip-end part thereof. For example, in a 27-Gauge ocular cutter, the deflection resistance of the shaft can be improved by forming the hardened layer 11 on the surface of the shaft so that the shaft does not lose the flexibility.

The present disclosure is also applicable to a stick-shaped extra-narrow member of an article other than the medical instrument 20. In a metal article provided with a stick-shaped extra-narrow metal member which has a thickness of 1 mm or less (particularly 0.5 mm or less), the deflection resistance of the extra-narrow member can be improved by forming the hardened layer 11 on the surface of the extra-narrow member so as not to lose the flexibility. Such a metal article may include metal terminals, pins, screws, precision gauges, precision tools, precision jigs, etc.

Moreover, the present disclosure is also applicable to a linear extra-narrow member. In a metal article provided with a linear extra-narrow metal member which has a thickness of 1 mm or less (particularly 0.5 mm or less), the deflection resistance of the extra-narrow member can be improved by forming the hardened layer 11 on the surface of the extra-narrow member so that the extra-narrow member does not lose the flexibility. Such a metal article may include medical catheters, guide wires, stents, etc.

Moreover, the present disclosure is also applicable to an extra-thin member. In a metal article provided with an extra-thin metal member which has a thickness of 1 mm or less (particularly 0.5 mm or less), the deflection resistance of the extra-thin member can be improved by forming the hardened layer 11 on the surface of the extra-thin member so that the extra-thin member does not lose the flexibility. Such a metal article may include metal terminals, precision gauges, precision tools, precision jigs, capacitors, etc.

Moreover, the present disclosure is also applicable to a minute member. In a metal article provided with a minute metal member having a maximum size of 1 mm or less (particularly 0.5 mm or less) in length and width, the hardened layer 11 may be formed on the surface of the minute member. According to the present disclosure, the minute member which does not conventionally have the hardened layer can be improved in the hardness. Such a metal article may include fine precision components, vacuum components, electronic components, fuel cell components, cell components, MEMS, optical components, etc.

INDUSTRIAL APPLICABILITY

The present disclosure is applicable to a medical instrument etc. provided with an extra-narrow metal member.

DESCRIPTION OF REFERENCE CHARACTERS

10 Ophthalmic Medical Device (Medical Device)
11 Hardened Layer, Nitrided Layer
20 Ocular Forceps (Medical Instrument)
21 Shaft
22 Core
23 Tip-End Part
30 Handle

The invention claimed is:

1. Medical ocular forceps comprising:
 a tubular shaft made of either an austenitic stainless steel or a cobalt-chromium-nickel alloy and having a thickness-wise diameter of not greater than 0.5 mm; and
 a core rod axially reciprocatingly inserted inside the tubular shaft, the core rod configured with a forceps tip exposed through a tip end of the tubular shaft and openable/closable by axial reciprocation of the core rod; wherein
 the tubular shaft is exterior-surface nitrided, carburized, or carbonitrided to impart to the tubular shaft a predetermined flexibility satisfying the following three-point bending test conditions under an ambient temperature of 20° C.±0.5° C.:
 with the tubular shaft supported on two fulcrums spaced 30 mm apart, the compression load applied orthogonally to the longitudinal center of the tubular shaft to yield 3-mm downward deflection is between 0.5N and 1.0N.

2. The medical ocular forceps of claim 1, wherein the tubular shaft is nitrided, carburized, or carbonitrided to a thickness of 2 μm or more and 18 μm or less.

3. The medical ocular forceps of claim 1, wherein the tubular shaft is exterior-surface nitrided or carburized in such a way as to be superficially in the S-phase.

4. The medical ocular forceps of claim 1, wherein the tubular shaft is exterior-surface carbonitrided in such a way as to be superficially in the S-phase.

5. A medical device, comprising:
 the medical ocular forceps of claim 1; and
 a handle to which the medical ocular forceps is attached.

6. The medical ocular forceps of claim 1, wherein the shaft has a thickness of 27 Gauge.

* * * * *